(12) United States Patent
Qing et al.

(10) Patent No.: US 11,037,662 B2
(45) Date of Patent: Jun. 15, 2021

(54) MEDICAL MONITORING SYSTEM, METHOD OF DISPLAYING MONITORING DATA, AND MONITORING DATA DISPLAY DEVICE

(71) Applicant: Shenzhen Mindray Bio-Medical Electronics Co., Ltd., Shenzhen (CN)

(72) Inventors: Lei Qing, Shenzhen (CN); Qinglin Tao, Shenzhen (CN); Shuaijun Liu, Shenzhen (CN); Yande He, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 0 days.

(21) Appl. No.: 15/949,856

(22) Filed: Apr. 10, 2018

(65) Prior Publication Data

US 2018/0277243 A1     Sep. 27, 2018

Related U.S. Application Data

(63) Continuation of application No. PCT/CN2015/091665, filed on Oct. 10, 2015.

(51) Int. Cl.
*G16H 10/60*     (2018.01)
*A61B 5/00*     (2006.01)
(Continued)

(52) U.S. Cl.
CPC ............. *G16H 10/60* (2018.01); *A61B 5/339* (2021.01); *A61B 5/745* (2013.01); *A61B 5/7435* (2013.01); *G06F 3/04847* (2013.01); *G16H 40/63* (2018.01); *G16H 50/30* (2018.01); *A61B 2505/03* (2013.01); *G06F 2203/04803* (2013.01)

(58) Field of Classification Search
CPC ................................ G16H 10/60; A61B 5/044
See application file for complete search history.

(56) References Cited

U.S. PATENT DOCUMENTS 8,568,327 B2 * 10/2013 O'Brien ............... A61B 5/0476
                                                    600/483
9,113,193 B1 *  8/2015 Gardes ............... H04N 21/4113
(Continued)

FOREIGN PATENT DOCUMENTS

| CN | 101939738 | 1/2011 |
| CN | 202288276 | 7/2012 |
| CN | 104798074 | 7/2015 |

*Primary Examiner* — Amy M Levy
(74) *Attorney, Agent, or Firm* — Kory D. Christensen

(57) ABSTRACT

A medical monitoring system includes: one or more signal sampling devices to detect parameter data corresponding to at least one physiological parameter; memory to store the parameter data corresponding to the at least one physiological parameter; a display to display parameter data obtained by at least one sensor; and a processor to obtain, according to the parameter data, abnormal event indications having a plurality of different attributes and transmit the abnormal event indications to the display; wherein the abnormal event indications are shown as anomalies identifiers on a timeline.

20 Claims, 9 Drawing Sheets

(51) Int. Cl.
*G16H 50/30* (2018.01)
*G16H 40/63* (2018.01)
*A61B 5/339* (2021.01)
*G06F 3/0484* (2013.01)

(56) References Cited

U.S. PATENT DOCUMENTS

| | | | |
|---|---|---|---|
| 10,303,850 B2* | 5/2019 | Kurami | G16H 50/70 |
| 2008/0126989 A1* | 5/2008 | Flores | H04N 21/8193 |
| | | | 715/833 |
| 2009/0005703 A1* | 1/2009 | Fasciano | A61B 5/031 |
| | | | 600/561 |
| 2009/0158326 A1* | 6/2009 | Hunt | H04N 5/783 |
| | | | 725/38 |
| 2011/0173193 A1* | 7/2011 | Ahn | G06F 16/2428 |
| | | | 707/725 |
| 2011/0201911 A1* | 8/2011 | Johnson | A61B 5/1495 |
| | | | 600/365 |
| 2011/0320976 A1* | 12/2011 | Piersol | G06F 3/0488 |
| | | | 715/810 |
| 2012/0042246 A1* | 2/2012 | Schwesinger | G06F 3/04855 |
| | | | 715/716 |
| 2013/0032147 A1* | 2/2013 | Robinson | A61M 16/021 |
| | | | 128/204.18 |
| 2014/0075380 A1* | 3/2014 | Milirud | G06F 11/323 |
| | | | 715/810 |
| 2014/0275819 A1 | 9/2014 | Kassem | |
| 2015/0248534 A1* | 9/2015 | Krzywicki | G06F 3/04842 |
| | | | 715/771 |
| 2017/0014090 A1* | 1/2017 | Tsugo | G09G 5/18 |

* cited by examiner

MEDICAL MONITORING SYSTEM, METHOD OF DISPLAYING MONITORING DATA, AND MONITORING DATA DISPLAY DEVICE

CROSS-REFERENCE TO RELATED APPLICATIONS

This application is a continuation of PCT Application No. PCT/CN2015/091665, filed Oct. 10, 2015, for MEDICAL INTENSIVE CARE SYSTEM, METHOD OF DISPLAYING INTENSIVE CARE DATA, AND INTENSIVE CARE DATA DISPLAY DEVICE, which is incorporated herein by reference.

TECHNICAL FIELD

The present disclosure relates to the field of medical monitoring systems, and in particular to a medical monitoring system, a method of displaying monitoring data, and a monitoring data display device.

BACKGROUND ART

Patient monitoring systems are commonly used, for example, in intensive care units (ICUs) of hospitals to monitor physiological states of patients. A common patient monitoring system is a bedside monitoring device having one or more sensors disposed on the patient to sense parameter data, such ECG, blood pressure, blood oxygen, blood glucose, and temperature. The parameter data can be displayed on a video display or stored for subsequent analysis.

When health care personnel review historical parameter data of the patient with a monitoring device, they generally need to browse parameter change conditions of the patient over a past period of time so as to find anomalous or key change time points for inspection. Conventional monitoring devices generally present historical data of the patient with one window, and the health care personnel adjust the contents of the historical data of the patient displayed in the window by adjusting a sampling interval or window time interval of the historical data of the patient displayed in the window. A defect of this method is that the health care personnel cannot observe parameter data change conditions of the patient outside the selected time interval of the display window when inspecting with a smaller data sampling interval, e.g., shorter window time interval. Likewise, when inspecting a greater data sampling interval, e.g., longer window time interval, although the health care personnel can observe the parameter data change conditions over a wider time range, information about these anomalous or key change time points is not displayed in sufficient detail, which causes the health care personnel to frequently switch between different data sampling intervals or window time intervals, making browsing operations inconvenient.

SUMMARY

To solve the aforementioned problems, a medical monitoring system, a method of displaying monitoring data, and a monitoring data display device are provided. In one embodiment, a medical monitoring system may include: a memory; one or more signal sampling devices to detect parameter data corresponding to at least one physiological parameter; a display to display the parameter data obtained by the one or more signal sampling devices; and a processor to obtain, according to the parameter data, instructions of anomalous events with a plurality of different attributes, and transmit the instructions of the anomalous events to the display; wherein one or more anomalies identifiers corresponding to the anomalous events are displayed on a monitoring timeline according to the attributes of the anomalous events.

In one embodiment, a method of displaying monitoring data may include: obtaining parameter data of at least one physiological parameter; obtaining, according to the parameter data, anomalous events with a plurality of different attributes; and displaying, according to the attributes of the anomalous events, one or more anomalies identifiers corresponding to the anomalous events in a monitoring timeline.

In one embodiment, a display device may include: a memory to store at least one physiological parameter and parameter data corresponding to the at least one physiological parameter; a display to display the parameter data; and a processor to obtain, according to the parameter data, instructions of anomalous events with a plurality of different attributes, and transmit the instructions of the anomalous events to the display; wherein one or more anomalies identifiers corresponding to the anomalous events are displayed in the entire monitoring time interval of a timeline according to the attributes of the anomalous events.

The medical monitoring system, method of displaying monitoring data, and monitoring data display device enhance convenience for users, such as health care personnel, to inspect parameter data of a patient in a historical monitoring time interval, greatly improving the user experience.

DETAILED DESCRIPTION

The monitoring system disclosed in the embodiments of the present disclosure is able to continuously present physiological parameter states of a monitored patient in a clear and concise manner, which is convenient for health care personnel to browse and inspect historical physiological parameter data of the patient and handle anomalous events occurring in a monitoring time interval.

In various embodiments of the present disclosure, the monitoring system has a touch display screen with a GUI, one or more processors, and a memory including one or more modules, programs or instruction sets for executing multiple functions. In various embodiments of the present disclosure, these functions may include remote video conferencing, picture/graphic browsing, a pathological database, calendar information, patient file information display, patient directory information display, etc. The modules, programs or instructions for executing the functions may be contained in a computer program product for one or more processors to execute the modules, programs or instructions.

In various embodiments of the present disclosure, the monitoring system may be embodied in medical multi-function monitoring equipment having a touch screen or touch display screen. The touch display screen may support a variety of applications using an intuitive GUI (GUI). The GUI can be implemented with a computer language, such as Visual Basic (VB) or Java, which generates graphical objects displayed in the GUI, wherein the graphical object includes one or a combination of graphics, text, pictures, etc. displayed on the GUI.

An application or function utilizing a gesture input of the touch display screen may be used. Alternatively, a hardware input apparatus (e.g., click wheel, keyboard, mouse, and/or joystick) may also be included to execute an operation similar to the above gesture input on the GUI, for example, a cursor is controlled by the hardware input apparatus to move on the GUI to generate an operation action presented on the GUI similar to the gesture input.

An environment in which the various embodiments of the present disclosure may operate is introduced in detail in conjunction with the accompanying drawings. In the following detailed description, many specific details are provided for comprehensive understanding of the embodiments of the present disclosure. However, for those of ordinary skill in the art, it is apparent that the present disclosure may also be implemented without these specific details. In other cases, well-known methods, processes, components, circuits and networks are not described in detail to avoid obscuring the inventive aspects.

Figure 1:
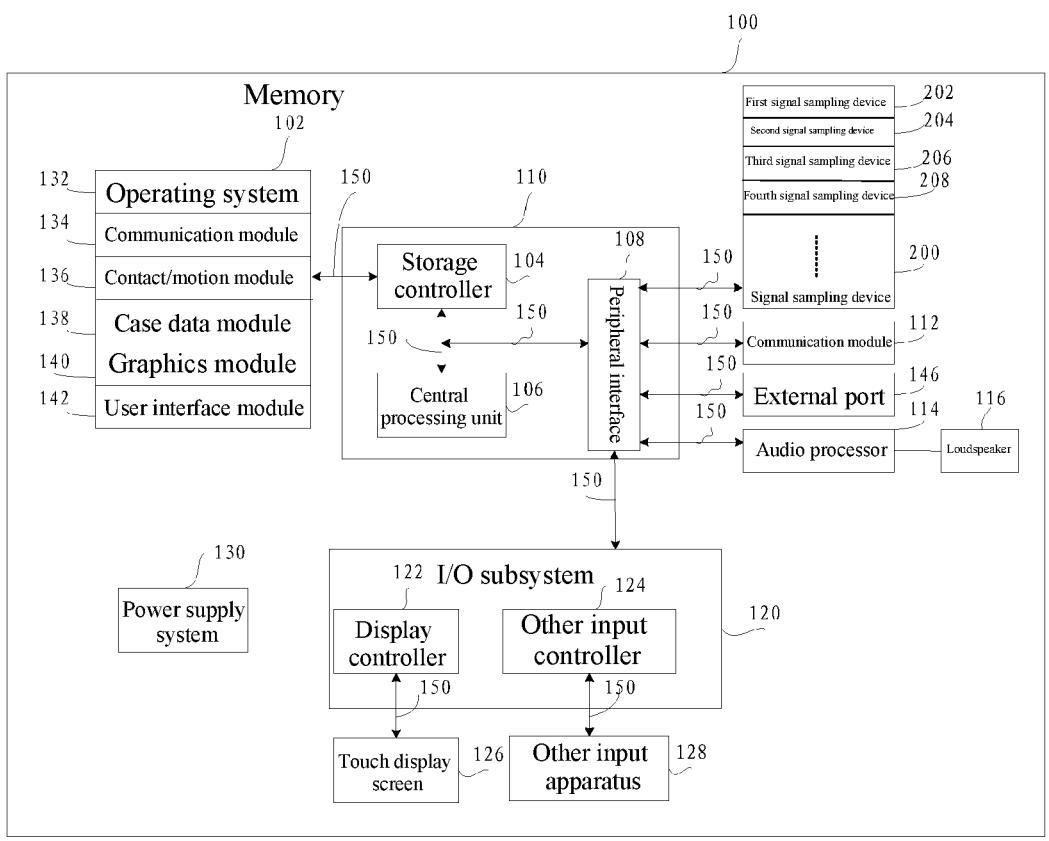
FIG. 1 is a schematic architectural diagram of a medical monitoring system according to some embodiments.

Referring to FIG. 1, a functional structural block diagram is shown of a medical monitoring system 100 with a touch display screen 126. The monitoring system 100 may include a memory 102 including one or more computer readable storage mediums, a storage controller 104, a central processing unit 106 (which may include one or more processors and/or controllers), a peripheral interface 108, an I/O subsystem 120, a display controller 122, a touch display screen 126, other input apparatus controller 124 and other input apparatus 128. The monitoring system 100 may further include a communication module 112, an audio processor 114, a loudspeaker 116, a signal sampling device 200, an external port 146 and a power supply system 130 (including a DC/DC conversion circuit and/or an AC/DC conversion circuit). The above various elements or modules may intercommunicate on one or more communication buses or signal lines 150.

The memory 102 may include a high-speed random access memory, and may also include a non-volatile memory, such as one or more magnetic disk storage devices, flash memory devices, or other non-volatile solid-state storage devices. In some embodiments, the memory 102 may further include storage remote from the one or more processors 106, such as network attached memory accessed via the communication module 112 or the external port 146 and a communication network (not shown), which may include the Internet, one or more internal networks, a local area network (LAN), a wide area network (WAN) and a storage area network (SAN), etc., or an appropriate combination thereof. The storage controller 104 may control the access to the memory 102 from other assemblies such as the CPU 106, the peripheral interface 108 and the like of the monitoring system 100.

The peripheral interface 108 couples input and output peripherals connected to the monitoring system 100 with the central processing unit 106. The central processing unit 106 runs or executes various software programs and/or instruction sets stored in the memory 102 so as to execute various functions and applications of the monitoring system 100 and process data.

In various embodiments of the present disclosure, the peripheral interface 108, the central processing unit (CPU) 106 and the storage controller 104 may be implemented, for example, on a single chip 110. In some embodiments, they may also be implemented on a plurality of separate chips.

The communication module 112 is configured to receive a communication signal, convert the same into an electrical signal and convert the electrical signal into a communication signal to transmit. The communication module 112 may be implemented using known techniques and enables the monitoring system 100 to communicate with an external network or other external apparatus. For example, the communication module 112 can connect to the Internet and Intranet of the World Wide Web (WWW) and/or a wireless and/or wired network such as a cellular telephone network, a local area network (LAN) and/or a metropolitan area network (MAN) to communicate with other systems and devices. The communication module 112 can use any one of a variety of communication standards, protocols and techniques, including but not limited to utilizing a wired or wireless medium, including Bluetooth, Ethernet, 802.11(x), a body area network or other wireless protocols.

The audio processor 114 and the loudspeaker 116 provide an audio interface between users (health personnel) and the monitoring system 100. The audio processor 114 may receive audio data from the peripheral interface 108, convert the audio data into an electrical signal, and send the electrical signal to the loudspeaker 116. The loudspeaker 116 converts the electrical signal into sound waves which can be heard by humans. The peripheral interface 108 may retrieve audio data from the memory 102 and/or the communication module 112 and/or send audio data to the memory 102 and/or the communication module 112.

The I/O subsystem 120 couples the touch display screen 126 and the other input apparatus 128 with the peripheral interface 108. The I/O subsystem 120 may include the display controller 122 and one or more other input controllers 124 to control the other input apparatus 128. The one or more other input controllers 124 receive/send an electrical signal from/to the other input apparatus 128. The other input apparatus 128 may include an actual button and a similar apparatus, a drive plate, a slide switch, a joystick, a click wheel, etc. In some embodiments of the present disclosure, the one or more other input controllers 128 can be coupled with any one or more apparatus of a keyboard, an infrared port, a USB port and a mouse, for example.

The touch display screen 126 provides a gesture input interface between the monitoring system 100 and the user, wherein the gesture input interface is implemented mainly by means of a GUI object of a virtual button, soft keyboard, etc. provided on the GUI of the touch display screen 126. The display controller 122 sends an electrical signal to the touch display screen 126 and/or receives an electrical signal from the touch display screen 126. The touch display screen 126 displays a visualized output to the user. The visualized output may include one or a combination of more of a graphic, text, an icon, a picture, etc., which are collectively referred to as a "graphic" herein.

The touch display screen 126 has at least one touch-sensitive surface to receive a gesture input from the user according to touch and/or contact. The display controller 122 calls a relevant module and/or instruction set in the memory 200 to provide a GUI by displaying graphics on the touch display screen 126, detects a gesture input from the user sensed by the touch-sensitive surface, and converts the detected gesture input into a GUI object (such as one or more soft keys, icons or buttons) displayed on the touch display screen 126, so as to realize interaction between the touch display screen 126 and the user. In an embodiment of the present disclosure, the contact operation position between the touch display screen 126 and the user corresponds to the contact position of a direct contact between an input object, such as a user finger, and the touch display screen 126, or a mapping position of the spatial position when the input object, such as a user finger, approaches the touch display screen 126 mapped onto the touch display screen 126.

The touch display screen 126 may use an LCD (liquid crystal display) technique or LPD (luminescent polymer display) technique but may also use other display techniques in other embodiments. The display screen in the touch display screen 126 and the display controller 122 may utilize any one of a variety of touch sensing techniques which are currently known or will be developed in the future to detect the contact in the gesture input and any motion or interruption thereof, these touch sensing technique including but not limited to capacitance, resistance, infrared, surface acoustic wave techniques, image recognition-based or data glove-based gesture input techniques, and a sensor array or other elements for determining the proximity between the input object and one or more contact points on the surface of the touch display screen 126.

The monitoring system 100 further includes a power supply system 130 for providing a power input for various elements or modules or circuits, which includes a power management system, one or more power sources (such as a battery and alternating current (AC)), a charging system, a power failure detection circuit, a power converter or inverter, a power state indicator (for example, a light emitting diode (LED)), and any other components relevant to the generation, management and distribution of power in the monitoring system 100. According to different power sources, the power supply system may contain a DC/DC conversion circuit or contain an AC/DC conversion circuit.

The monitoring system 100 may further include a signal sampling device 200, and the signal sampling device 200 detects at least one physiological parameter related to a monitored object and obtains parameter data corresponding to the at least one physiological parameter. The at least one piece of physiological parameter data (biological information) related to the monitored object may be multi-monitoring parameter data (information) related to the electrocardiogram (ECG), non-invasive blood pressure (NIBP), heart rate (HR), oxyhemoglobin saturation (SpO2), carbon dioxide ($CO_2$), body temperature, cardiac output, pulse rate and anesthetic gas analysis, etc. The signal sampling device 200 includes one or more one or more signal sampling devices related to the above plurality pieces of physiological parameter data (information). FIG. 1 shows a signal sampling device 202 to sample an electrocardiogram signal, a second signal sampling device 204 to sample a blood pressure signal, a third signal sampling device 206 to sample the pulse rate, and a fourth signal sampling device 208 to measure the body temperature, etc. which are coupled with the peripheral interface 108. In this embodiment, the signal sampling device 200 includes sensors for directly sampling signals corresponding to physiological parameters and a signal processor to process the signals sampled by the sensors. In addition to the parameter data measured via the signal sampling device 200, patient information further includes any or all information in the case, including but not limited to statistical information, such as the patient's name, bed number, patient identification number (ID) or the ID of the doctor in charge of the patient. The patient information may further include the patient's height, weight, family medical history, laboratory reports, etc.

In some embodiments, the memory 102 includes an operating system 132, a communication module (or instruction set) 134, a contact/motion module (instruction set) 136, a case data module (or instruction set) 138, a graphics module (or instruction set) 140 and a user interface display module 142.

The operating system 132 (such as Linux, Unix, OS, Windows or an embedded system like VxWorks) includes various software components and/or drivers which are to control and associate conventional system tasks (such as memory association, storage device control and power supply management) and facilitate communication between various software and hardware.

The communication module 134 is helpful to communicate with other apparatuses or systems via one or more external ports 146, and further includes various software modules to process data received by the external port(s) 146. The external port 146, such as a universal serial bus (USB), FireWire, etc., is appropriate for being directly or indirectly via a network (such as the Internet, a wireless LAN, etc.) coupled with other apparatuses or systems.

The contact/motion module 136 and the touch screen display controller 122 together detect the contact with the touch screen 126. The contact/motion module 136 includes various software components to execute various operations associated with contact detection with the touch screen 126. The operations may include, for example, determining whether there is a contact, determining whether the contact is moving, and tracking the movement on the touch screen 126 and determining whether the contact is interrupted (i.e. whether the contact is stopped). The operation of determining the movement of a contact point may include determining the rate (amplitude), velocity (amplitude and direction) and/or acceleration (including the amplitude and/or direction) of the contact point.

The graphics module 140 includes various known software components to present and display graphics on the touch screen 126. It should be noted that "graphics" may include any object that can be displayed to a user, including but not limited to text, icons (for example, a user interface object including a software key), digital images, waveforms, numerical values, etc.

In some embodiments, the user interface module 142 is to control the display of a GUI of the monitoring system 100. When the user interface module 142 detects one or more instructions satisfying any one condition for GUI display, then the corresponding graphical interface is switched to for display. More details related to the GUI will be described hereinafter.

FIG. 1 above only refers to a structural block diagram of a medical monitoring system 100, such as a bedside patient monitor. The monitoring system 100 may also have more or fewer elements or modules than FIG. 1 and may also use two or more elements or modules above in combination or may also perform arrangement of different configurations on the architecture in FIG. 1. The various elements or modules shown in FIG. 1 may be implemented in the form of hardware, software, or a combination of hardware and software, including one or more signal processing and/or application-specific integrated circuits (ASICs).

The monitoring system 100 may remotely display and inspect medical data obtained by medical detection equipment, for example, the medical data herein may include any one piece of data that can be selected according to user requirements of medical image data, detection data (such as a blood pressure monitoring result, and an electrocardiogram detection result) obtained by various detection instruments and configuration parameters corresponding to the various detection instruments. With regard to the medical image data, the functions of video playback, picture viewing, image editing (such as commenting, classifying, cutting, pixel adjusting, etc.), video editing (such as remarking, noise removal, video length adjustment, playing effect adjustment, etc.) and medical image data transmission, etc. may be remotely performed by the monitoring system 100. The monitoring system 100 may further remotely control medical detection equipment, for example, receive medical image data and control information fed back by the medical detection equipment via the communication module 112, and/or send a control instruction to the medical detection equipment. The above medical detection equipment may be any one medical detection equipment that can obtain organism image data or sample medical parameter data, such as magnetic resonance imaging (MRI) equipment, ultrasound detection equipment, a blood sample analysis instrument, etc.

The monitoring system 100 may have a plurality of GUI states. The GUI states may be states that the monitoring system 100 responds to a user's input in a predetermined manner. In some embodiments, the plurality of GUI states includes display interfaces of parameter data of a current monitoring time interval and parameter data of a historical time interval. The so-called time interval herein refers to a time period.

Figure 2:
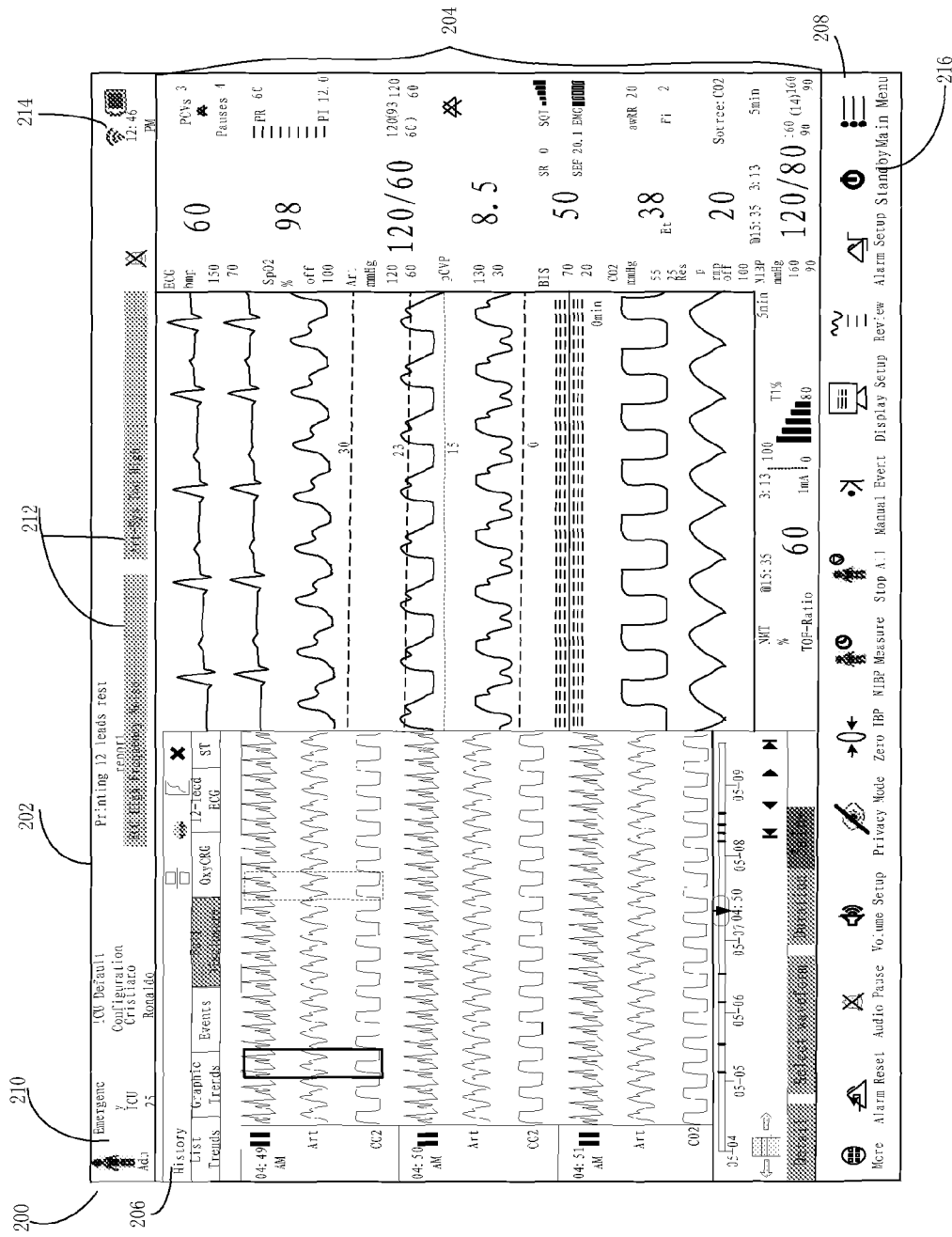
FIG. 2 is a schematic diagram of a graphical user interface (GUI) of a medical monitoring system according to some embodiments.

FIG. 2 is a schematic diagram of a GUI of some embodiments of the present disclosure. The GUI 200 shown in FIG. 2 presents information about parameter data of a current monitoring time interval and a historical monitoring time interval. In some embodiments, the GUI 200 includes: a first region 202, a second region 204, a third region 206 and a fourth region 208. In some embodiments, the first region 202 includes the top of the GUI. The second region 204 and the third region 206 are displayed in the middle of the GUI. In some embodiments, the fourth region 208 includes the bottom of the GUI.

In some embodiments, the first region 202 includes a patient information region 210, displaying the number of an ICU (Intensive Care Unit) where a patient is located, etc., an anomaly label region for important physiological parameters 212 and a current monitoring time region 214. In some embodiments, the anomaly label region for important physiological parameters 212 further includes a button for printing a 12-lead electrocardiogram and an important physiological parameter sampling anomaly label, and the important physiological parameter sampling anomaly label includes but is not limited to ECG high-frequency noise and too high systolic pressure (Art Sys Too High). The current monitoring time region 214 includes but is not limited to whether to turn on a sound identifier, a current monitoring time interval, a network connection state and an electric quantity identifier of the monitoring system 100, etc.

In some embodiments, the second region 204 is provided in the middle of the GUI. The second region 204 includes parameter data of the current monitoring time interval. The parameter data is represented in the form of waveforms and numerical values. In some embodiments, an upper left part of the second region 204 displays parameter data in waveforms, and an upper right part and the bottom of the second region 204 display parameter data in the form of data and percentages. There may also be other forms of the arrangement of waveforms and numerical values, which are not limited to the description of this embodiment.

In some embodiments, the third region 206 includes but is not limited to a left front part displayed in the second region 204 in a superposed manner. The third region 206 displays historical parameter data according to a period represented by an inspecting label. The third region 206 will be described in detail in combination with FIGS. 3 to 8. In some embodiments, the fourth region 208 further includes a menu region. The menu region further includes at least one menu icon or button 216. The display form of the GUI can be via at least one menu icon or button 216, for example, a display setup (Display setup) button, a privacy mode (Privacy Mode) button, a standby mode (Standby) button, an audio pause (Audio Pause) button and a volume setup (Volume Setup) button.

The parameter data in the historical monitoring time interval that are displayed in the third region 206 of the GUI 200 are illustrated by referring to FIGS. 3 to 8.

Figure 3:
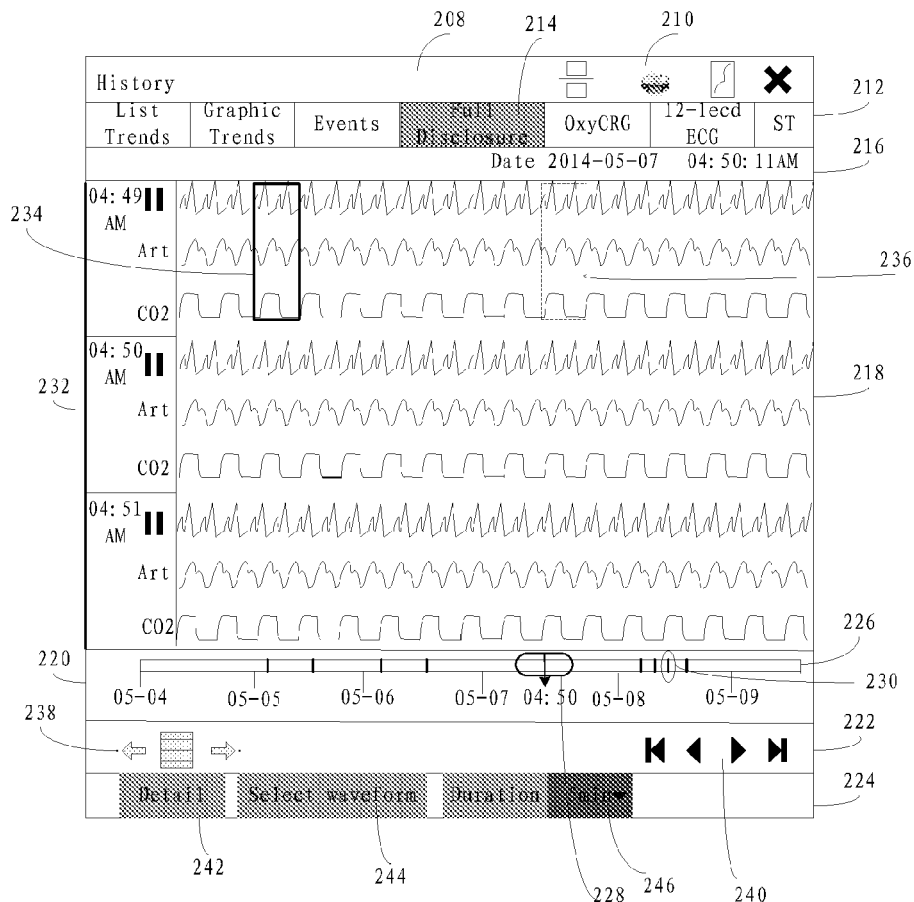
FIG. 3 is a schematic diagram of a GUI of a historical monitoring time interval of a medical monitoring system according to some embodiments.

In some embodiments, as shown in FIG. 3, the third region 206 includes a title region 208, a menu region 212, a waveform display region 218, a historical monitoring time interval region 220, a monitoring time selection region 222, and a configuration menu region 224. The title region 208 is provided at the top of a GUI 300, and a menu region 212 and a current monitoring time region 216 are successively arranged below the menu region 212 and occupy an upper middle region of the GUI 300. A waveform/data display region 218 is provided in the middle of the third region 206, the historical monitoring time interval region 220 and the monitoring time selection region 222 are successively arranged below the waveform display region 218, and the configuration menu region 224 is provided at the bottom of the third region 206.

In some embodiments, the title region 208 further includes at least one shortcut icon 210, the at least one shortcut 210 being a printer identifier, a close identifier, etc. The menu region 212 includes at least one parameter data display mode icon or button 214, and the at least one parameter data display mode icon or button 214 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and an ST segment button. In this embodiment, parameter data in the historical monitoring time interval are displayed in the form of a holographic waveform (Full Disclosure). In this embodiment, the waveform display region 218 displays the parameter data in the historical monitoring time interval in the form of waveforms in a holographic waveform (Full Disclosure) mode.

In some embodiments, the historical monitoring time interval region 220 includes a main timeline 226 (or a time axis, an overall timeline, or an overall time axis, the same below), a main inspecting label 228 provided on the main timeline 226, and one or more anomalies identifiers 230 for representing anomalous events. In an embodiment, the main timeline 226 (a monitoring timeline) corresponds to an entire monitoring time period of a single patient up to current time, and the anomalous events are anomalous events occurring according to all monitoring parameters that happen within the monitoring time period.

In some embodiments, the main timeline 226 indicates the whole time length from the starting of the monitoring of a patient to the current monitoring time. In some embodiments, the main timeline 226 can be displayed as a linear or elongated shape, for example, a horizontal long strip as shown in FIG. 3. In addition, when the display controller 122 receives no input instruction, the main timeline 226 will be hidden in one embodiment.

In some embodiments, when the display controller 122 receives an input instruction from users (health care personnel) through the main timeline 226, the main inspecting label 228 is positioned to a nearest anomalies identifier 230. In other words, a user input instruction at a particular point on the monitoring timeline may be detected, after which an anomalous event closest in time to the particular point is selected and the display of historical parameter data may be centered on the selected anomalous event. This is done in recognition that health care professionals may be primarily concerned about viewing details of anomalous events and the closest ones in time to a particular time of interest. The input time point can be any moment or time clip in the historical monitoring time interval of the main timeline 226. When the users (health care personnel) inspect parameter data on the main timeline 226, the waveform display region 218 displays parameter data corresponding to the main inspecting label 228.

In some embodiments, the main inspecting label 230 is sleeved on the main timeline 226 and can move along the main timeline 226. In this embodiment, a user (monitoring personnel) may utilize his or her finger on the touch display screen 126 or the other input apparatus 128, for example but not limited to a mouse, a handle, a keyboard, a joystick, a click wheel, etc. to control the main inspecting label 228, so as to selectively inspect monitoring moments corresponding to the main inspecting label 228.

In some embodiments, the main inspecting label 228 is displayed as a slide bar/slide block, and the width of the main inspecting label 228 is greater than that of the horizontal long strip for representing a main timeline 226. In this way, it is convenient for the health care personnel to select monitoring time through the touch display screen 126. The parameter data of the monitoring time clip corresponding to the main inspecting label 228 are inspected by moving the main inspecting label 228. In this embodiment, the downward arrow of the main inspecting label 228 indicates the historical monitoring time point corresponding to the main inspecting label 228, for example, 05-07, 04:50. In one embodiment, the downward arrow of the inspecting label may represent a middle monitoring time point of the inspecting period. At the same time, the time corresponding to the main inspecting label 228 is also synchronously displayed in the part 216. The parameter data in the time clip of the monitoring moment corresponding to the main inspecting label 228 correspond to a time window 234 in the waveform display region 218.

The time window 234 represents the position and/or proportion of the time clip of the monitoring moment corresponding to the main inspecting label 228 in the historical monitoring time interval. With the movement of the main inspecting label 228, the time frame 234 also moves accordingly.

In some embodiments, the slide bar/slide block identifying the main inspecting label 228 can be lengthened or shortened, for example, the slide bar/slide block can be lengthened or shortened by the relative movement of two contact points detected on the touch display screen 126 in a horizontal direction. The length of the time clip corresponding to the monitoring moment of the main inspecting label 228 can be expanded by extending the slide bar/slide block. Likewise, the length of the time clip corresponding to the monitoring moment of the main inspecting label 228 can be shortened by shortening the slide bar/slide block.

In some embodiments, the main timeline 226 includes the anomalies identifier 230 for representing the anomalous events, displayed on the main timeline 226 when an anomaly occurs. The anomalous events include a physiological parameter warning, a manually labeled event when health care personnel find an anomaly, and a technical warning event relevant to patient parameter measurement, etc.

In some embodiments, according to different attributes of the anomalous events above, the anomalies identifier 230 are displayed as light strips in different colors and/or shapes. For example, the anomalies identifier 230 of different attributes may be displayed in different colors or patterns, and the durations of the anomalous events with different attributes are displayed in different shapes. In this embodiment, the length of the light strips is set according to the length of the durations of the anomalous events. For example, the longer the duration of an anomalous event is, the wider the vertical strip is. The light strips corresponding to the anomalies identifier 230 may also be set in other shapes according to different attributes of the anomalous events.

Figure 4:
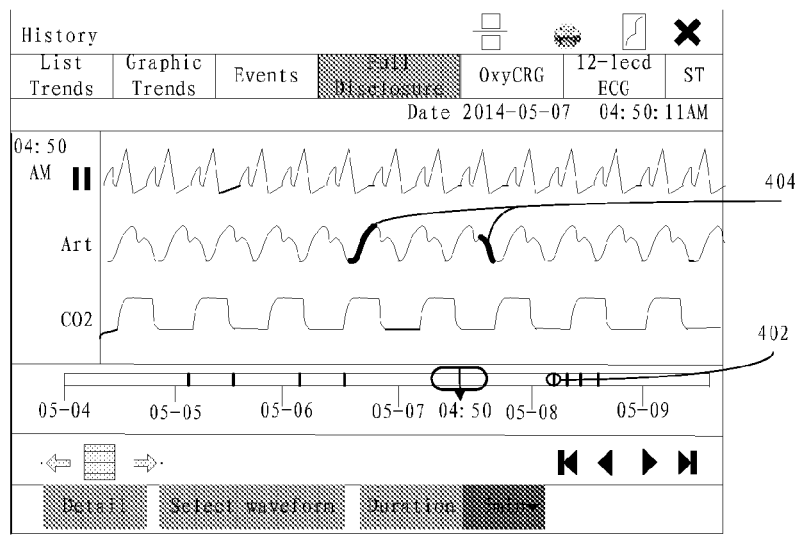
FIG. 4 is a schematic diagram of a GUI of a historical monitoring time interval of a medical monitoring system according to some embodiments.

In some embodiments, the color of each time point on the main timeline 226 indicates the change of a parameter trend value. For example, when the parameter data value changes from a low magnitude to a high magnitude, the color changes from green to red (not shown). In some embodiments, as shown in FIG. 4, the parameter data is displayed in the form of a parameter trend line on the main timeline 226, and the parameter data corresponding to the anomalies identifier 402 are displayed in different shapes and/or colors on the parameter trend line. In this embodiment, the parameter data corresponding to the anomalies identifier 402 are displayed in different colors on the parameter trend line, as indicated by 404. In addition, the parameter data corresponding to the anomalies identifier 402 may also be displayed in dashed lines of different colors, bold lines or other lines.

In some embodiments, an anomalies identifier 230 may serve as a link for jumping (or positioning) to detailed parameter data. For example, when the anomalies identifier 230 on the third region 206 are selected through the touch display screen 126 or other input apparatus 128, the waveform display region 218 directly displays the parameter data corresponding to the time clip of the monitoring moment of the main inspecting label 228. In an embodiment, an anomalies identifier 230 may be configured to inquire into an electronic case of a patient. For example, when the anomalies identifier 230 is selected through the touch display screen 126 or other input apparatus 128, same can be directly linked to and displayed in the electronic case, which is stored in the memory 102, of a monitored patient.

In some embodiments, the monitoring time selection region 222 includes an icon or button 238 for selecting the form of an inspecting time clip and a fast forward/rewind icon or button 222. For example, the parameter data in the historical monitoring time interval can be quickly inspected in a fast forward/rewind manner by clicking the fast forward/rewind icon or button 222.

In some embodiments, the configuration menu region 224 includes a detailed information pull-down menu button 242, a waveform selection pull-down menu button 244 and a time clip pull-down menu 246. The detailed information pull-down menu button 242 further includes detailed information about the monitored patient. The waveform selection (Select waveform) pull-down menu button 244 further includes different physiological parameter data displayed in waveforms. Other physiological parameter data can be selected by clicking the waveform selection pull-down menu button 244. In this embodiment, as shown in FIG. 4, displayed are IT carbon dioxide (CO2) and Art waveform. The time clip pull-down menu 246 includes time clip buttons/icons in the monitoring moments corresponding to main inspecting labels 228 of different lengths. For example, the length of the time clip can be as several minutes, a few hours, a day or a week.

In some embodiments, the third region 206 further includes a local timeline 232. The parameter data corresponding to the time clip are displayed on the local timeline 232.

Figure 5:
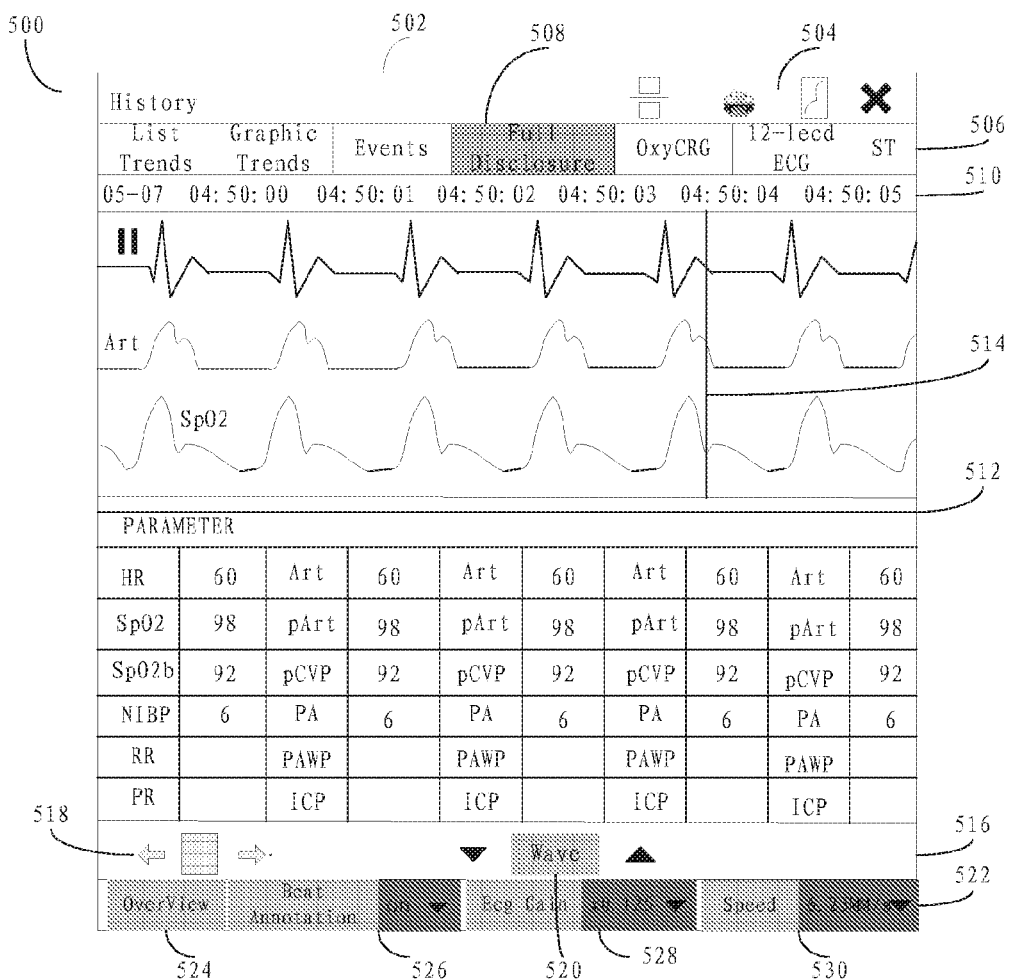
FIG. 5 is a schematic diagram of a GUI of a historical monitoring time interval of a medical monitoring system according to some embodiments.

FIG. 5 is a schematic diagram which displays a GUI 500 of the third region 206 in the form of a holographic waveform (Full Disclosure) according to some embodiments of the present disclosure.

In some embodiments, the GUI 500 includes a title region 502, a menu region 506, a local timeline region 510, a waveform/data display region 512, a configuration menu selection region 516 and a waveform display configuration region 522. The title region 502 is provided at the top of the GUI 500, and the menu region 506 and the local timeline region 510 are successively arranged below the menu region 506 and occupy an upper middle part of the GUI 500. The waveform/data display region 512 is provided in the middle of the GUI 500, the configuration menu selection region 516 is provided at a lower middle part of the GUI 500, and the waveform display configuration region 522 is provided at the bottom of the GUI 500.

In some embodiments, the title region 502 further includes at least one shortcut icon 504, the at least one shortcut 504 being a printer identifier, a close identifier, etc. The menu region 506 includes at least one parameter data display mode icon or button 508, and the at least one parameter data display mode icon or button 408 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and an ST segment button. In this embodiment, parameter data in a historical monitoring time interval are displayed in a holographic waveform (Full Disclosure).

In some embodiments, the local timeline region 510 includes the time clip of the monitoring moment corresponding to the main inspecting label 228. In some embodiments, the waveform/data display region 512 displays the parameter data in the time clip of the monitoring moment corresponding to the main inspecting label 228 in the form of waveforms and data. In this embodiment, parameter data corresponding to the time clip are displayed in a holographic waveform. The user may touch the waveform displayed in the waveform/data display region 512 to select a time point, after which the numerical values of corresponding parameters may be displayed in the table. In addition, a line 514 corresponds to selected time point may be displayed in the waveform/data display region 512.

In some embodiments, the configuration menu selection region 516 includes a local time selection button 518 and a waveform selection pull-down menu button 520. Different local time clips in the historical monitoring time interval can be selected by clicking a forward or backward identifier button of the local time selection button 518. The waveform selection pull-down menu button 520 may display waveforms of different physiological parameter data. In this embodiment, the waveform data include waveform data of Ecg, Art and SpO2.

In some embodiments, the waveform display configuration region 522 includes an overview (Overview) button 524, a beat annotation (Beat Annotation) pull-down menu button 526, an electrocardiogram gain (Ecg Gain) pull-down menu button 528, and a play speed (speed) pull-down menu button 530. In some embodiments, the beat annotation pull-down menu button 526 includes "on" and "off", and in this embodiment, it is labeled as "on". The Ecg gain multiples can be selected through the electrocardiogram gain pull-down menu button 528, and in this embodiment, the Ecg gain is 0.125 times. The play speed of the waveforms in the historical monitoring time interval can be set by the play speed pull-down menu button 530, and in this embodiment, the play speed is 6.25 MM/s.

Figure 6:
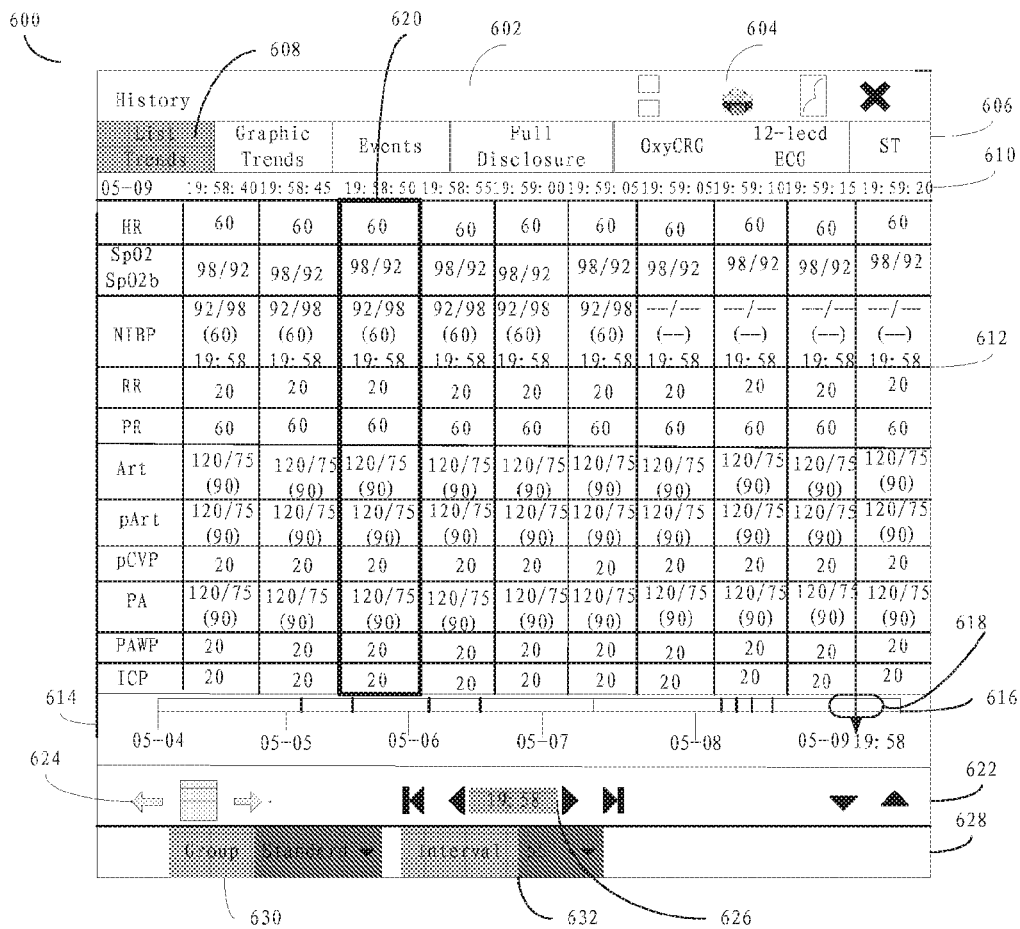
FIG. 6 is a schematic diagram of a GUI of a historical monitoring time interval of a medical monitoring system according to some embodiments.

FIG. 6 is a schematic diagram of a GUI 600 of the third region 206 in the form of a list trend (List Trend) according to some embodiments of the present disclosure. The list trend refers to a numerical table of parameter data in the entire monitoring time interval. In some embodiments, the GUI 600 includes a title region 602, a menu region 606, a local timeline region 610, a data display region 612, a main timeline region 614, a local time clip configuration region 622 and a data display configuration region 628. The title region 602 is provided at the top of the GUI 600, and the menu region 606 and the local timeline region 610 are successively arranged below the title region 602 and occupy an upper middle part of the GUI 600. The data display region 612 is provided in the middle of the GUI 600, the main timeline region 616 is provided at a lower middle part of the GUI 600, and the data display configuration region 628 is provided at the bottom of the GUI 600.

In some embodiments, the title region 602 further includes at least one shortcut icon 604, the at least one shortcut 604 being a printer identifier, a close identifier, etc. The menu region 606 includes at least one parameter data display mode icon or button 608, and the at least one parameter data display mode icon or button 608 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and an ST segment button. In this embodiment, parameter data in the historical monitoring time interval are displayed in the form of a list trend (List Trend).

In some embodiments, the local timeline region 610 includes the time clip of the historical monitoring time interval corresponding to the main inspecting label 618. In some embodiments, the data display region 612 displays the parameter data in the time clip of the historical monitoring time interval corresponding to the main inspecting label 618 in the form of data. In this embodiment, the list trend (List Trend) displays parameter data in the time clip in the form of numerical values. The parameter data in the monitoring moment corresponding to the main inspecting label 618 are shown in the time frame 620.

In some embodiments, the main timeline region 614 includes a timeline 616 and the main inspecting label 618 is slidably sleeved on the timeline 616.

In some embodiments, the local time clip configuration region 622 includes a local inspecting label 626 for adjusting the local timeline. In this embodiment, the local inspecting label 626 is displayed in the form of the fast forward and rewind icon. In addition, the local timeline can be adjusted by detecting the horizontal movement method of a contact point on the touch display screen 126. For example, the contact point when detected as moving to the right indicates an increasing local time, and the contact point moving to the left indicates decreasing local time. When the local time period is adjusted by the local inspecting label 626, a data frame 620 moves with the adjustment of the local time period.

In some embodiments, the data display configuration region 628 includes a group (Group) pull-down menu button 630, a time interval (Interval) pull-down menu button 632. In some embodiments, the group (Group) pull-down menu button 630 includes a standard display, etc. The time interval of displaying the parameter data is set by the time interval (Interval) pull-down menu button 632, and in this embodiment, the time interval is set as 5 s.

Figure 7:
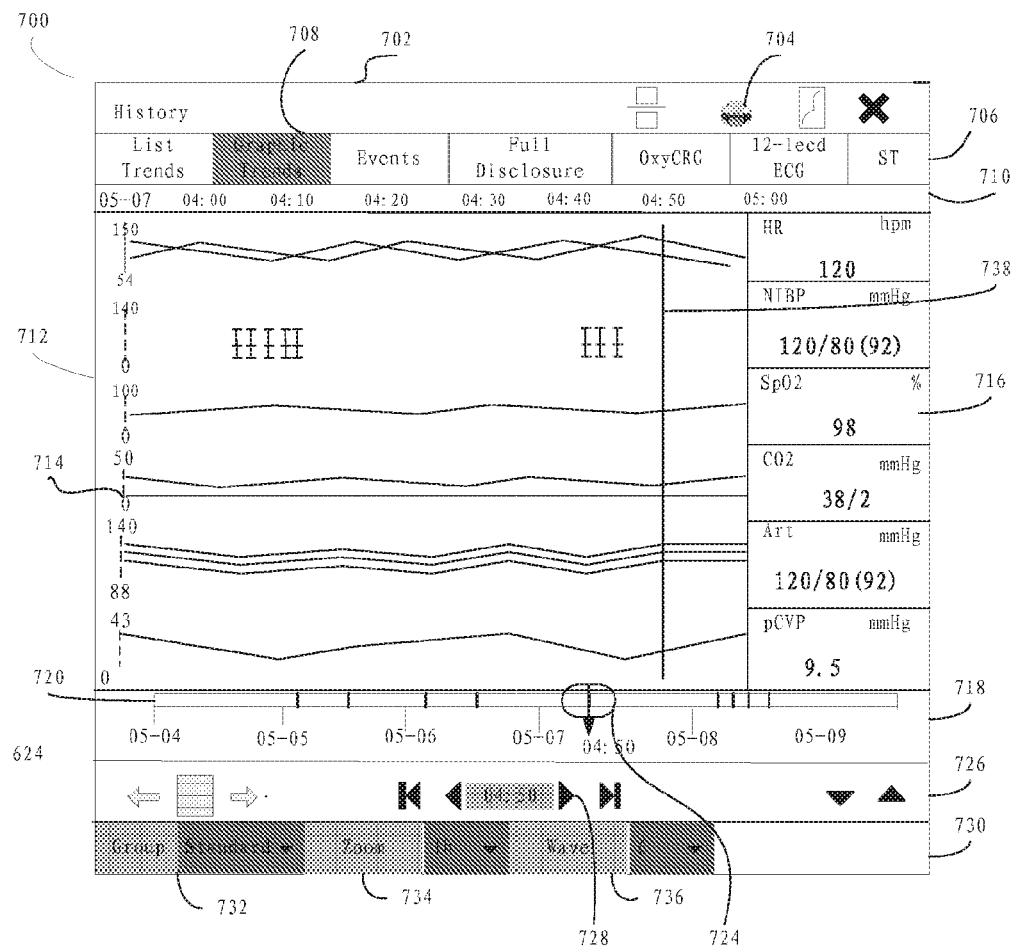
FIG. 7 is a schematic diagram of a GUI of a historical monitoring time interval of a medical monitoring system according to some embodiments.

FIG. 7 is a schematic diagram of a GUI 700 of the third region 206 in the form of a graphic trend (Graphic Trend) according to some embodiments of the present disclosure. In some embodiments, the GUI 700 includes a title region 702, a menu region 706, a local timeline region 710, a waveform data display region 712, a main timeline region 718, a local time clip configuration region 726 and a waveform display configuration region 730. The title region 702 is provided at the top of the GUI 700, and the menu region 706 and the local timeline region 710 are successively arranged below the title region 702 and occupy an upper middle part of the GUI 700. The waveform data display region 712 is provided in the middle of the GUI 700, the main timeline region 718 is provided at a lower middle part of the GUI 700, and the waveform display configuration region 730 is provided at the bottom of the GUI 700.

In some embodiments, the title region 702 further includes at least one shortcut icon 704, the at least one shortcut 704 being a printer identifier, a close identifier, etc. The menu region 706 includes at least one parameter data display mode icon or button 708, and the at least one parameter data display mode icon or button 708 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and an ST segment button. In this embodiment, the parameter data in the historical monitoring time interval are displayed in the form of a waveform graphic trend (Graphic Trend).

In some embodiments, the local timeline region 710 includes the time clip of the historical monitoring time interval corresponding to the main inspecting label 724. In some embodiments, the waveform data display region 712 includes a waveform region 714 and a data region 716. The waveform region 714 and the data region 716 respectively display the parameter data of the time clip in a historical monitoring time interval corresponding to the main inspecting label 724 in the form of waveforms and numerical values.

In some embodiments, the main timeline region 718 includes a timeline 720 and the main inspecting label 724 slidably sleeved on the timeline 720.

In some embodiments, the local time clip configuration region 726 includes a local inspecting label 728 for adjusting the local timeline. In this embodiment, the local inspecting label 728 is displayed in the form of the fast forward and rewind icon. When the local time period is adjusted by the local inspecting label 728, the local time clip displayed in the local timeline region 710 will be updated accordingly, and a vertical line 738 of the waveform region 714 will move accordingly.

In some embodiments, the graphic display configuration region 730 includes a group (Group) pull-down menu button 732, a zoom in/out (Zoom) pull-down menu button 734, and a waveform (Wave) pull-down menu button 736. In some embodiments, the group (Group) pull-down menu button 732 includes a standard display, etc. In some embodiments, the zoom in/out (Zoom) pull-down menu button 734 can set the length of the displayed local time clip. In this embodiment, the length of the local time clip is 8 h. Waveforms corresponding to different parameter data can be selected by the waveform (Wave) pull-down menu button 736.

Figure 8:
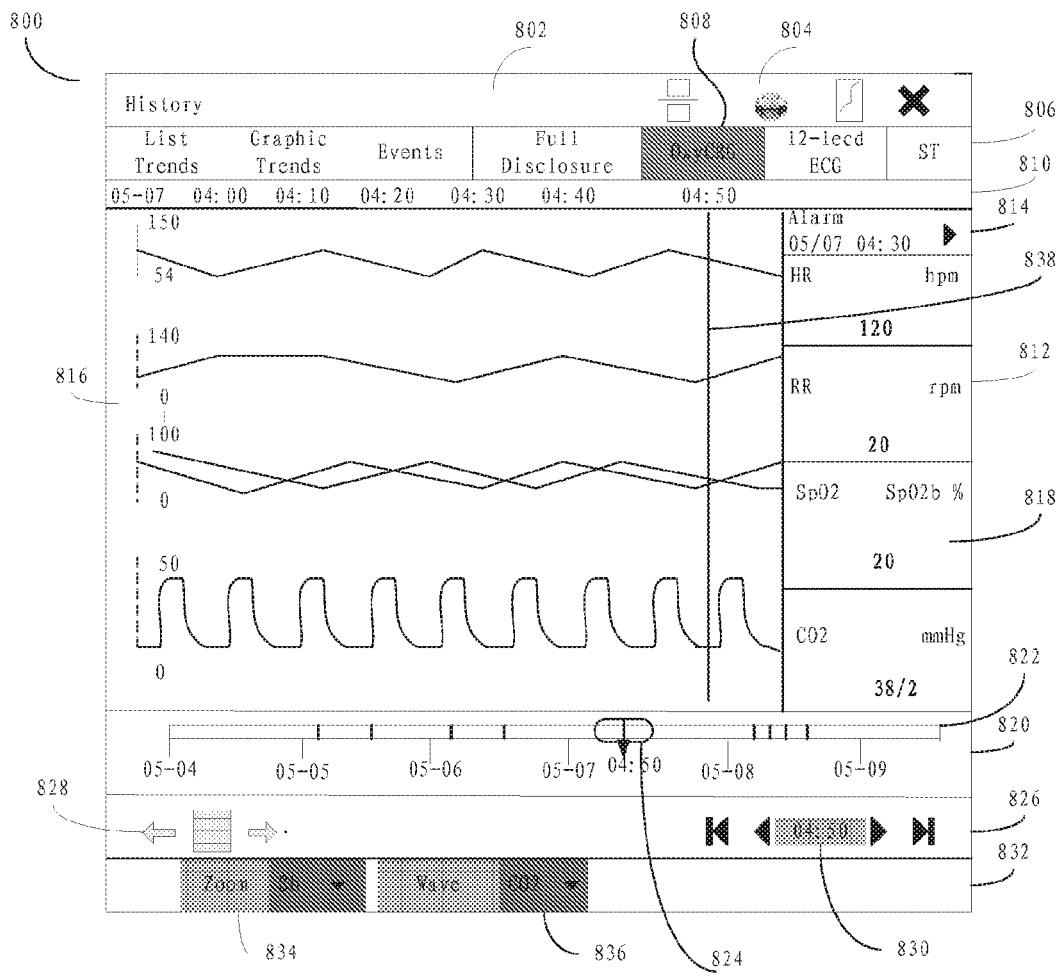
FIG. 8 is a schematic diagram of a GUI of a historical monitoring time interval of a medical monitoring system according to some embodiments.

FIG. 8 is a schematic diagram of a GUI 800 of the third region 206 in the form of respiratory oxygenation (OxyCRG) according to some embodiments of the present disclosure. In some embodiments, the GUI 800 includes a title region 802, a menu region 806, a local timeline region 810, a waveform data display region 812, a main timeline region 820, a local time clip configuration region 826 and a waveform display configuration region 832. The title region 802 is provided at the top of the GUI 800, and the menu region 806 and the local timeline region 810 are successively arranged below the title region 802 and occupy an upper middle part of the GUI 800. The waveform data display region 812 is provided in the middle of the GUI 800, the main timeline region 820 is provided at a lower middle part of the GUI 800, and the waveform display configuration region 832 is provided at the bottom of the GUI 800.

In some embodiments, the title region 802 further includes at least one shortcut icon 804, the at least one shortcut 804 being a printer identifier, a close identifier, etc. The menu region 806 includes at least one parameter data display mode icon or button 808, and the at least one parameter data display mode icon or button 808 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and an ST segment button. In this embodiment, parameter data in the historical monitoring time interval are displayed in the form of respiratory oxygenation (OxyCRG).

In some embodiments, the local timeline region 810 includes the time clip of the historical monitoring time interval corresponding to the main inspecting label 824. In some embodiments, the waveform data display region 812 includes a waveform region 816 and a data region 818. The waveform region 816 and the data region 818 respectively display the parameter data in the time clip of the historical monitoring time interval corresponding to the main inspecting label 824 in the form of waveforms and data. An anomalous event region 814 closest to the time of the main inspecting label 824 is also identified in an upper left corner of the data region 818.

In some embodiments, the main timeline region 820 includes a timeline 822 and the main inspecting label 824 slidably sleeved on the timeline 820.

In some embodiments, the local time clip configuration region 826 includes a local inspecting label 828 for adjusting the local timeline and a fast forward/rewind button 830 for adjusting the monitoring time point of the current main inspecting label 824. When the local time period is adjusted by the local inspecting label 828, a vertical line 838 of the waveform region 816 will move accordingly.

In some embodiments, the graphic display configuration region 832 includes a zoom in/out (Zoom) pull-down menu button 834, and a waveform (Wave) pull-down menu button 836. In some embodiments, the zoom in/out (Zoom) pull-down menu button 834 can set the length of the displayed local time clip. In this embodiment, the length of the local time clip is 8 h. Waveforms corresponding to different parameter data can be selected by the waveform (Wave) pull-down menu button 836, and in this embodiment, the displayed waveform is the waveform corresponding to the parameter CO2.

Figure 9:
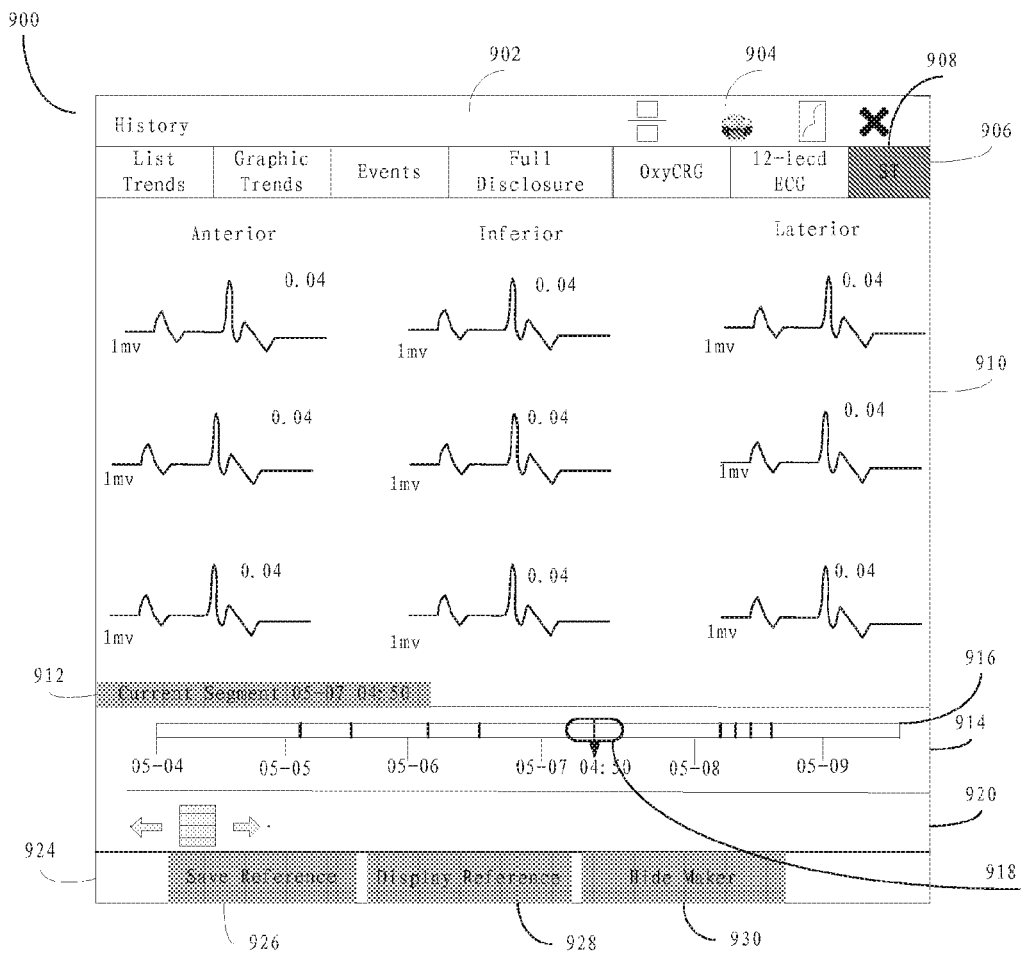
FIG. 9 is a schematic diagram of a GUI of a historical monitoring time interval of a medical monitoring system according to some embodiments.

FIG. 9 is a schematic diagram of a GUI 900 of the third region 206 in the form of an ST segment according to some embodiments of the present disclosure. In some embodiments, the GUI 900 includes a title region 902, a menu region 906, an ST segment waveform display region 910, a main timeline region 914, a local time clip configuration region 920 and a waveform display configuration region 924. The title region 902 is provided at the top of the GUI 900, and the menu region 906 is provided below the title region 902 and occupies an upper middle part of the GUI 900. The ST segment waveform display region 910 is provided in the middle of the GUI 900, the main timeline region 914 is provided at a lower middle part of the GUI 900, and the waveform display configuration region 924 is provided at the bottom of the GUI 900.

In some embodiments, the title region 902 further includes at least one shortcut icon 904, the at least one shortcut 904 being a printer identifier, a close identifier, etc. The menu region 906 includes at least one parameter data display mode icon or button 908, and the at least one parameter data display mode icon or button 808 further includes a list trend (List Trend) button, a graphic trend (Graphic Trend) button, an events (Events) button, a holographic waveform (Full Disclosure) button, a respiratory oxygenation (OxyCRG) button, a 12-lead ECG button and a button. In this embodiment, parameter data of the ST segment in the historical monitoring time interval are displayed.

In some embodiments, the ST segment waveform display region 910 includes a current monitoring time display region 912. In some embodiments, the main timeline region 914 includes a timeline 916 and a main inspecting label 918 slidably sleeved on the timeline 916.

In some embodiments, the waveform display configuration region 924 includes a save reference (Save Reference) 926, a display reference (Display Reference) button 928 and a hide maker button (Hide Maker) 930.

Figure 10:
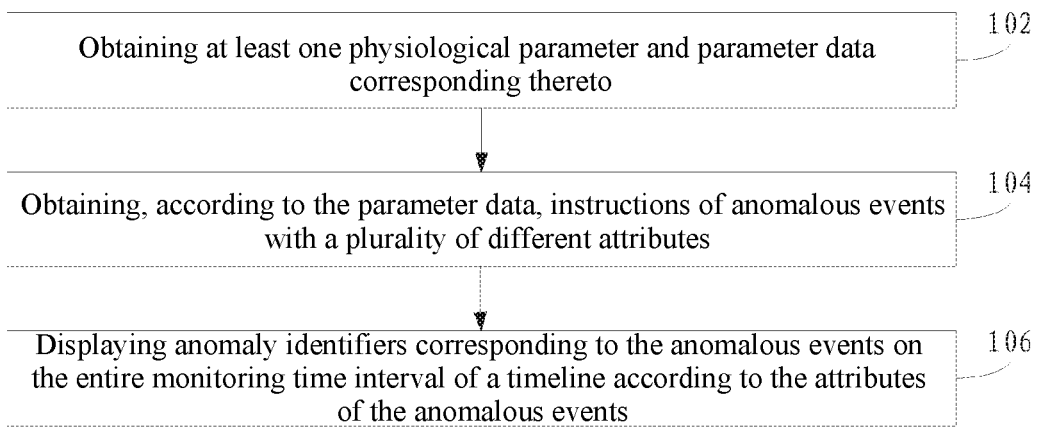
FIG. 10 is a flowchart of a method of displaying monitoring data according to some embodiments.

As shown in FIG. 10, a method of displaying monitoring data in some embodiments of the present disclosure includes the following steps:

Step 102, obtaining at least one physiological parameter and parameter data corresponding to the at least one physiological parameter;

Step 104, obtaining, according to the parameter data, anomalous events with a plurality of different attributes; and Step 106, displaying, according to the attributes of the anomalous events, anomalies identifier corresponding to the anomalous events displayed in the entire monitoring time interval of the timeline.

The specific implementations of step 102, step 104 and step 106 may refer to the description of the GUIs 200 to 900 heretofore provided.

Figure 11:
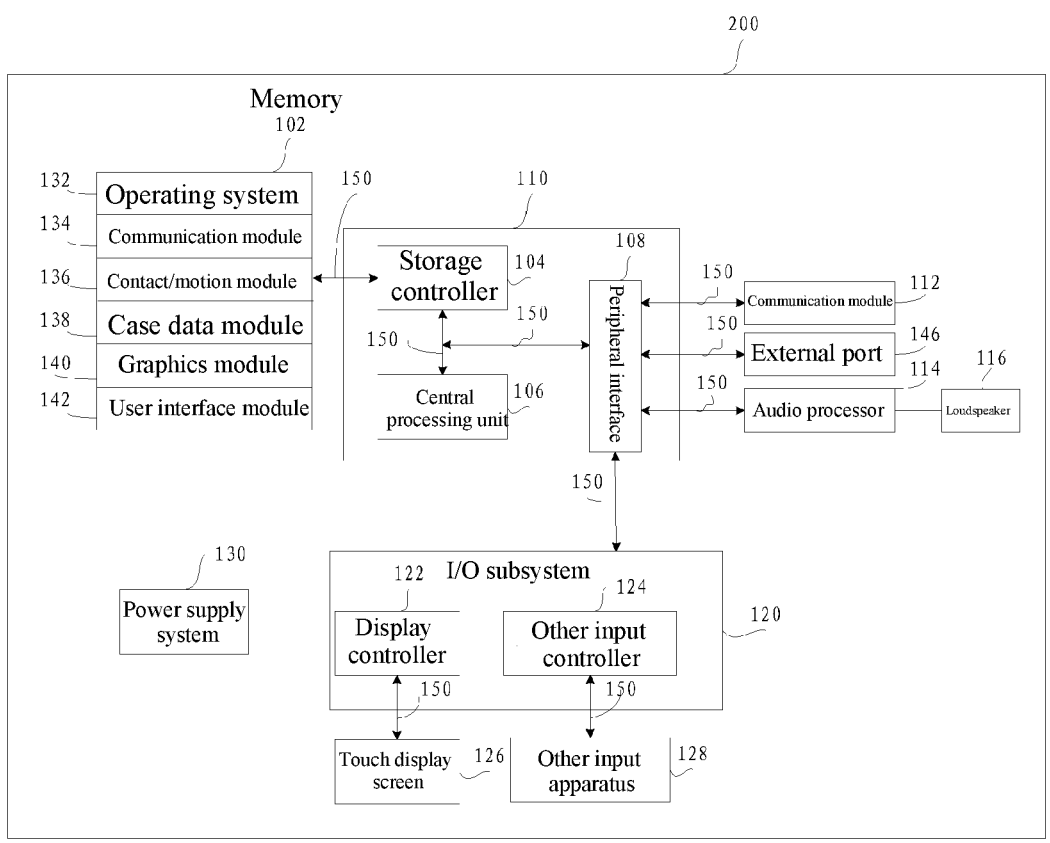
FIG. 11 is a structural block diagram of a monitoring data display device according to some embodiments.

As shown in FIG. 11, the monitoring display device 200 in some embodiments of the present disclosure may include a memory 102 including one or more computer readable storage mediums, a storage controller 104, a central processing unit 106 (which may include one or more processors and/or controllers), a peripheral interface 108, an I/O subsystem 120, a display controller 122, a touch display screen 126, other input apparatus controller 124, and other input apparatus 128. The monitoring system 100 may further include a communication module 112, an audio processor 114, a loudspeaker 116, a signal sampling device 200, an external port 146 and a power supply system 130 (comprising a DC/DC conversion circuit and/or an AC/DC conversion circuit). The above various elements or modules may intercommunicate on one or more communication buses or signal lines 150.

The description of various constituting parts of the monitoring data display device 200 may refer to the parts of the medical monitoring system 100. The specific display method of the GUI of the monitoring data display device 200 may refer to the description of the GUIs 200 to 900 heretofore described.

The medical monitoring system, method of displaying monitoring data, and monitoring data display device enhance convenience for users, such as health care personnel, to inspect parameter data of a patient in a historical monitoring time interval, greatly improving the user experience.

The above-mentioned examples merely represent several embodiments, giving specifics and details thereof, but should not be understood as limiting the scope of the present patent of disclosure thereby. It should be noted that those of ordinary skill in the art would also able to make several alterations and improvements without departing from the spirit of the present disclosure and these would all fall within the scope of protection of the present disclosure. Therefore, the protection scope of the present disclosure shall be subject to appended claims.

What is claimed is:

1. A medical monitoring system, comprising:
a memory that stores historical parameter data obtained from one or more signal sampling devices during a monitoring time period, the historical parameter data corresponding to at least one physiological parameter of a patient, wherein the memory further stores two or more indications of anomalous events occurring within the monitoring time period;
a display screen that displays, in a first area of a graphical user interface, a first timeline representing the monitoring time period, wherein the display screen further displays an anomalies identifier on the first timeline corresponding to each anomalous event, wherein the first timeline corresponds to an entire monitoring time period of a single patient up to a current time, and wherein the anomalous events are anomalous events occurring according to physiological parameters that happen within the monitoring time period;
an input apparatus to detect an input instruction in connection with the graphical user interface at a point on or near an anomalies identifier in the first timeline; and a processor to select, if the input instruction is on an anomalies identifier in the first timeline, an anomalous event corresponding to the anomalies identifier in the first timeline that is on the detected point of the input instruction; and to select automatically, if the input instruction is near but not on an anomalies identifier in the first timeline, an anomalous event corresponding to the anomalies identifier on the first timeline that is nearest in time to the detected point of the input instruction, wherein the processor positions an inspection label on the selected anomalous event in the first timeline;

wherein the display screen displays a second timeline in a second area of the graphical user interface, the second timeline comprising a first time period covering the selected anomalous event, a second time period nearest in time before the first time period and a third time period nearest in time after the first time period, wherein the first, second, and third time periods of the second timeline are displayed in separate horizontal rows representing subsets of the historical parameter data, wherein a movable time window is displayed on one of the horizontal rows at a point determined by the inspection label in the first timeline;

wherein the display screen further displays at least a portion of the historical parameter data as a waveform for the first time period covering the selected anomalous event in a first row, at least a portion of the historical parameter data as a waveform for the second time period in a second row and at least a portion of the historical parameter data as a waveform for the third time period in the third row; and wherein the first and second timelines are displayed simultaneously in separate regions of the graphical user interface.

2. The medical monitoring system of claim 1, wherein the at least a portion of the historical parameter data displayed in the second area is for a time period centered on the selected anomalous event.

3. The medical monitoring system of claim 1, wherein, in response to the input apparatus detecting an input instruction on a particular anomalies identifier, the display screen displays detailed historical parameter data concerning the anomalous event corresponding to the particular anomalies identifier.

4. The medical monitoring system of claim 3, wherein the detailed historical parameter data are displayed in the second area of the graphical user interface.

5. The medical monitoring system of claim 1, wherein the display screen displays the at least a portion of the historical parameter data in the form of one or more parameter trend lines; and wherein at least a portion of the displayed historical parameter data corresponding to a time of the selected anomalous event are displayed in a different color.

6. The medical monitoring system of claim 1, wherein the display screen displays each anomalies identifier on or near the timeline as a light strip.

7. The medical monitoring system of claim 6, wherein the light strips are perpendicular to the timeline.

8. The medical monitoring system of claim 6, wherein the display screen displays the first timeline as a horizontal strip; and wherein the light strips are embedded in the horizontal strip and horizontally aligned with the horizontal strip.

9. The medical monitoring system of claim 1, wherein the display screen displays the inspecting label as a slide block or slide bar;

wherein a length of the inspecting label corresponds to a length of a time period indicated by the inspecting label; and wherein the length of the time period is adjustable by lengthening or shortening the inspecting label based on input from the input apparatus.

10. The medical monitoring system of claim 1, wherein the first timeline is hidden when no input instruction is being received.

11. The medical monitoring system of claim 1, wherein the display screen displays, in a third area of the graphical user interface, a third timeline including current parameter data and wherein the first, second, and third timelines are displayed as not overlapped with each other in the graphical user interface.

12. The medical monitoring system of claim 1, wherein a horizontal length of the anomalies identifier is proportional to a duration of a corresponding anomalous event.

13. The medical monitoring system of claim 1, wherein the second timeline is adjustable into different time length.

14. The medical monitoring system of claim 1, wherein the different time length comprises several minutes, a few hours, a day or a week.

15. The medical monitoring system of claim 1, wherein the display screen further displays, in a third area of the graphical user interface, one or more current parameter data as a waveform up to the current time, and displays, in a fourth area of the graphical use interface, the one or more current parameter data in data or percentage up to the current time.

16. A method for patient monitoring, comprising:

storing historical parameter data obtained from one or more signal sampling devices during a monitoring time period, the historical parameter data corresponding to at least one physiological parameter of a patient;

storing two or more indications of anomalous events occurring within the monitoring time period;

displaying, in a first area of a graphical user interface, a first timeline representing the monitoring time period;

displaying an anomalies identifier on or near the first timeline corresponding to each anomalous event, wherein the first timeline corresponds to an entire monitoring time period of a single patient up to a current time, and the anomalous events are anomalous events occurring according to physiological parameters that happen within the monitoring time period;

detecting an input instruction at a point on the first timeline;

selecting, if the input instruction is on an anomalies identifier in the first timeline, an anomalous event corresponding to the anomalies identifier in the first timeline that is on the detected point of the input instruction; and automatically selecting, if the input instruction is near but not on an anomalies identifier in the first timeline, an anomalous event corresponding to the anomalies identifier on the first timeline that is nearest in time to the detected point of the input instruction;

positioning an inspection label on the selected anomalous event in the first timeline;

displaying a second timeline in a second area of the graphical user interface, the second timeline comprising a first time period covering the selected anomalous event, a second time period nearest in time before the first time period and a third time period nearest in time after the first time period, wherein the first, second, and third time periods of the second timeline are displayed in separate horizontal rows representing subsets of the historical parameter data, wherein a movable time window is displayed on one of the horizontal rows at a point determined by the inspection label in the first timeline; and wherein the first and second timelines are displayed simultaneously in separate regions of the graphical user interface.

17. The method of claim 16, wherein the at least a portion of the historical parameter data displayed in the second area is for a time period centered on the selected anomalous event.

18. The method of claim 16, wherein, in response detecting an input instruction on a particular anomalies identifier, displaying detailed historical parameter data concerning the anomalous event corresponding to the particular anomalies identifier.

19. The method of claim 18, wherein the detailed historical parameter data are displayed in the second area of the graphical user interface.

20. A non-transitory computer-readable storage medium comprising program code that, when executed by a processor, perform a method for patient monitoring, the method comprising:

storing historical parameter data obtained from one or more signal sampling devices during a monitoring time period, the historical parameter data corresponding to at least one physiological parameter of a patient;

storing two or more indications of anomalous events occurring within the monitoring time period;

displaying, in a first area of a graphical user interface, a first timeline representing the monitoring time period;

displaying an anomalies identifier on or near the first timeline corresponding to each anomalous event, wherein the first timeline corresponds to an entire monitoring time period of a single patient up to a current time, and the anomalous events are anomalous events occurring according to physiological parameters that happen within the monitoring time period;

detecting an input instruction at a point on or near the first timeline;

selecting, if the input instruction is on an anomalies identifier in the first timeline, an anomalous event corresponding to the anomalies identifier in the first timeline that is on the detected point of the input instruction; and automatically selecting, if the input instruction is near but not on an anomalies identifier in the first timeline, an anomalous event corresponding to the anomalies identifier on the first timeline that is nearest in time to the detected point of the input instruction, wherein the processor positions an inspection label on the selected anomalous event in the first timeline; and displaying a second timeline in a second area of the graphical user interface, the second timeline comprising a first time period covering the selected anomalous event, a second time period nearest in time before the first time period and a third time period nearest in time after the first time period, wherein the first, second, and third time periods of the second timeline are displayed in separate horizontal rows representing subsets of the historical parameter data, wherein a movable time window is displayed on one of the horizontal rows at a point determined by the inspection label in the first timeline; and wherein the first and second timelines are displayed simultaneously in separate regions of the graphical user interface.

* * * * *